(12) United States Patent
Licini et al.

(10) Patent No.: US 6,791,339 B2
(45) Date of Patent: Sep. 14, 2004

(54) METHOD AND APPARATUS FOR NONDESTRUCTIVE MEASUREMENT AND MAPPING OF SHEET MATERIALS

(75) Inventors: Jerome C. Licini, Mucungie, PA (US); Nikolai Eberhardt, Bethlehem, PA (US)

(73) Assignee: Lehighton Electronics, Inc., Lehighton, PA (US)

( * ) Notice: Subject to any disclaimer, the term of this patent is extended or adjusted under 35 U.S.C. 154(b) by 7 days.

(21) Appl. No.: 10/137,188

(22) Filed: May 1, 2002

(65) Prior Publication Data

US 2003/0016032 A1 Jan. 23, 2003

Related U.S. Application Data

(60) Provisional application No. 60/288,266, filed on May 3, 2001.

(51) Int. Cl.[7] .......................... G01R 27/04; G01R 31/26
(52) U.S. Cl. ........................ 324/642; 324/719; 324/765
(58) Field of Search ................................ 324/631, 632, 324/637, 639, 642, 765, 644, 648, 719, 207.13; 361/234

(56) References Cited

U.S. PATENT DOCUMENTS

| | | | |
|---|---|---|---|
| 4,087,745 A | * | 5/1978 | Kennedy et al. ............ 324/642 |
| 4,605,893 A | | 8/1986 | Braslau |
| 5,103,182 A | | 4/1992 | Moslehi |
| 5,196,786 A | | 3/1993 | Usami et al. |
| 5,781,018 A | | 7/1998 | Davidov et al. |
| 6,100,703 A | * | 8/2000 | Davidov et al. ............ 324/631 |

* cited by examiner

Primary Examiner—Albert DeCady
Assistant Examiner—James Kerveros
(74) Attorney, Agent, or Firm—Duane Morris LLP (57) ABSTRACT

An apparatus for contactless measurement of carrier concentration and mobility includes a microwave source, a circular waveguide for transmitting microwave radiation to a sample, such as a semiconductor wafer or panel for flat panel displays, at a measurement location, a first detector for detecting the forward microwave power, a second detector for detecting the microwave power reflected from the sample, and a third detector for detecting the Hall effect power. A circular waveguide, carrying only the TE11 mode, is terminated by the sample behind which a short is located. Perpendicular to the plane of the sample (and along the axis of the circular waveguide), a magnetic field is applied. In this configuration, a given incident TE11 wave will cause two reflected waves. One is the ordinary reflected wave in the same polarization as the incident one. A detector is provided to measure this reflected radiation. The other reflected wave is caused by the Hall effect. Its polarization is perpendicular to the former wave and a probe is provided to detect this as well. This reflected wave is detected by a probe, the output of which is combined with an attenuated and phase shifted portion of the forward radiation at a single detector.

15 Claims, 6 Drawing Sheets

METHOD AND APPARATUS FOR NONDESTRUCTIVE MEASUREMENT AND MAPPING OF SHEET MATERIALS

RELATED APPLICATIONS

This application claims priority from U.S. Provisional Patent Application No. 60/288,266, filed May 3, 2001, which application is hereby incorporated by reference in its entirety.

FIELD OF THE INVENTION

The invention described in this patent application relates to nondestructive measurement and mapping of materials, particularly using microwaves in the measurement of carrier concentration and mobility and sheet resistance in semiconductor wafers and flat panel displays.

BACKGROUND OF THE INVENTION

Existing instruments that employ microwaves in the measurement of sheet resistance in GaAs wafers employ an X-band waveguide configuration with a characteristic impedance of 300 ohms which does not permit accurate measurement of wafers with thin cap layers. Such instruments are discussed in U.S. Pat. No. 4,605,893, to Norman Braslau. One disadvantage of these instruments is an inability to separately measure the properties of multiple conducting layers in wafers that contain such layers, e.g. a high-electron-mobility transistor (HEMT) wafer, which contains a two-dimensional (2D) channel layer and a cap layer. Therefore, one must measure the sheet resistance and mobility at temperatures lower than 300 degrees Kelvin, such as at 77 degrees Kelvin, in such existing systems in order to increase the channel-layer mobility relative to the conductance of the cap layer. These instruments also require involved calibration procedures.

Destructive techniques for measurement of sheet resistance and mobility are also known. However, such techniques necessarily damage the wafers or other material being measured.

SUMMARY OF THE INVENTION

A device for nondestructive measurement of mobility and carrier concentration in sheet materials includes a microwave source, a circular waveguide configured to transmit microwaves received from the microwave source to a conductive sheet material, such as a semiconductor wafer or flat panel display, a first detector for receiving the forward microwave power, a second detector for detecting the microwave power reflected from the material, and a third detector for detecting the Hall effect power. A circular waveguide, carrying only the TE11 mode, is terminated by the wafer behind which, at a distance of ¼ wavelength, a short is located. Perpendicular to the plane of the wafer (and along the axis of the waveguide), a variable magnetic field is applied. In this configuration, a given incident TE11 wave will cause two reflected waves. One is the ordinary reflected wave in the same polarization as the incident one. This is used to measure sheet resistance. The other reflected wave is caused by the Hall effect. Its polarization is perpendicular to the former wave and this can be separately detected with a properly configured probe.

A device for measurement of mobility and carrier concentration in conductive sheet materials includes a microwave source; a circular waveguide positioned to receive microwave radiation from the microwave source; a mount adapted to position a sheet material item at a measurement location to receive microwave radiation transmitted from the circular waveguide; a magnet positioned to induce a magnetic field at the measurement location; a first detector positioned to detect the power of the microwave radiation source; a second detector positioned to detect the power of the microwave radiation reflected from a sheet material item in the measurement location; and a third detector positioned to detect a Hall effect microwave power. A fourth detector may be provided to detect magnetic field strength at the measurement location.

A method for measurement of mobility and carrier concentration in conductive sheet materials includes generating microwave radiation; transmitting only the TE11 mode of the generated microwave radiation successively to a conductive short and to a sheet material sample; during the step of transmission, applying a magnetic field of selected intensity; detecting microwave field strength at a forward position; detecting microwave field strength reflected from each of the conductive short and the sample; detecting Hall effect microwave field strength; and, based on the detected microwave field strengths, calculating values for mobility and carrier concentration.

DETAILED DESCRIPTION

The present invention includes an apparatus and method for measurement of sheet resistance and carrier concentration in conductive materials. The device includes a microwave source, that has an output coupled to a waveguide configuration in which a small amount of the incident wave is diverted, and the greater portion of the incident wave is transmitted along a main branch. The main branch is coupled to a circular waveguide. The circular waveguide transmits only the TE11 (transverse electric 1, 1) mode of the microwave radiation. The circular waveguide receives radiation at a interface, and outputs radiation to a test region having a mount for supporting either a conductive test item, such as a short, or a wafer or other conductive sheet item to be tested. A magnetic is provided to apply a magnetic field at the test region. At least four values are detected in the calculation of sheet resistance and carrier concentration in a method and apparatus of the invention. A detector is provided to detect the total microwave power output. A second detector is provided to detect the strength of a conventional reflected wave in the same polarization as the incident wave. A third detector is provided to detect a second reflected wave having a polarization opposite to that of the incident wave. There is preferably provided a Hall effect probe to detect this reflected wave, which probe is electrically coupled to a directional coupler. The diverted portion of the incident wave, after passing through an attenuator and a phase shifter, is also coupled to this Hall directional coupler for calibration purposes. The Hall directional coupler is then coupled to a detector. A fourth detector detects the magnetic field strength.

Figure 1:
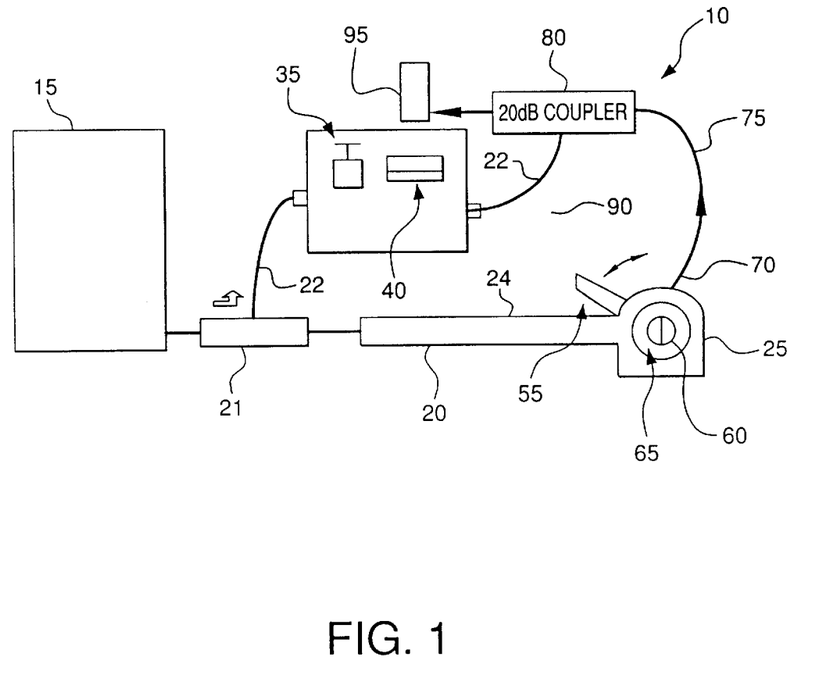
FIG. 1 is a schematic diagram of an apparatus according to the invention.
Figure 2:
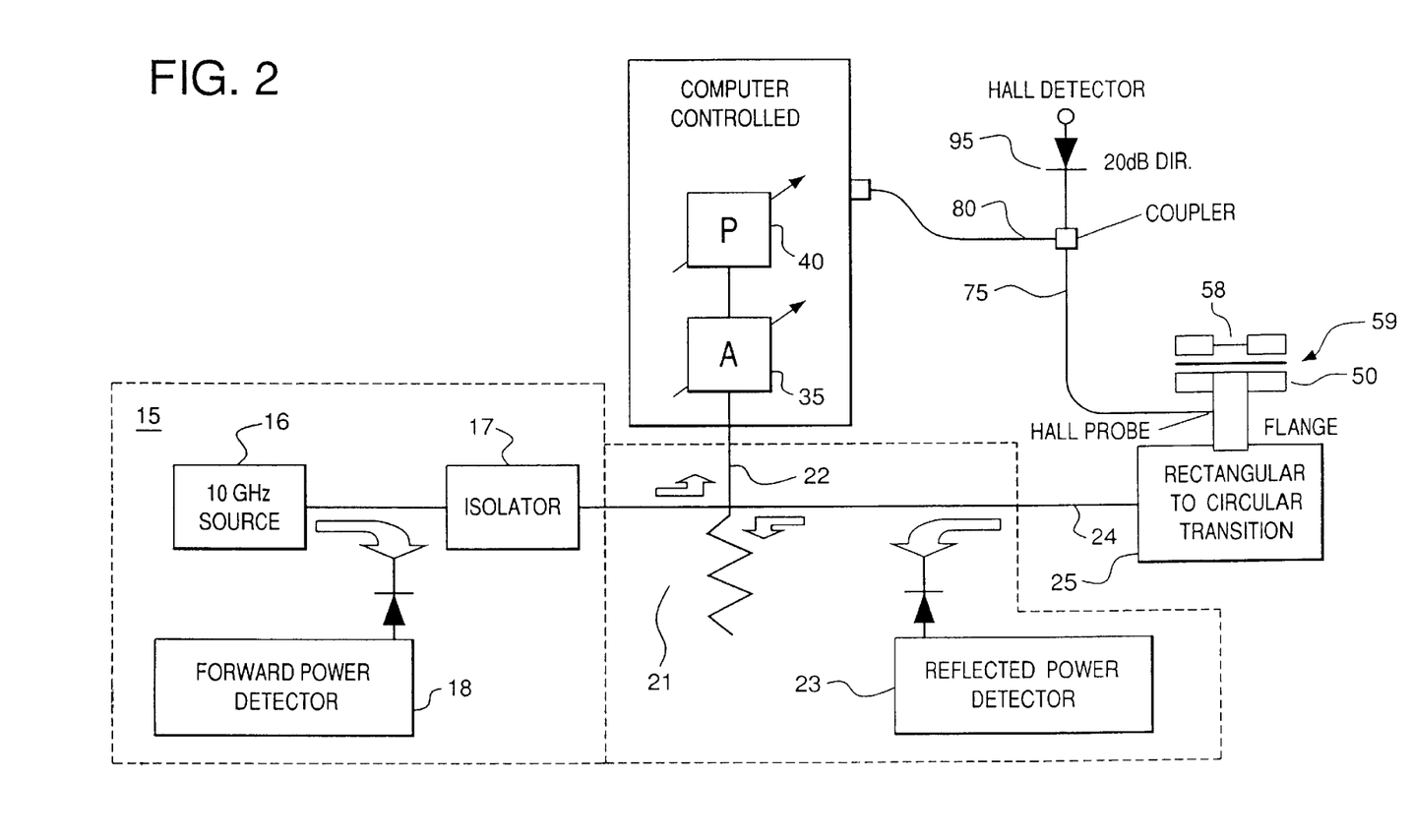
FIG. 2 is a schematic diagram of an apparatus according to the invention.

FIGS. 1 and 2 depict schematically the components of an apparatus 10 in accordance with the invention. Apparatus 10 includes microwave source module 15 which may provide microwaves having a frequency of about 10 GHz, although other frequencies may be employed. For example, higher frequencies may be employed to enable a smaller measurement area on the wafer or other item being tested. Source module 15 may include a Gunn diode, for example, and other sources may be employed. Source module 15 includes the microwave source 16, such as a Gunn diode, which is coupled through a waveguide to isolator 17. Isolator 17 may be of conventional or other suitable design to prevent radiation from elsewhere in apparatus 10 from entering source 15. Source module 15 further includes a power detector 18, for detecting the intensity of the microwave field. Detector 18 is also referred to as the forward power detector.

The output of source module 15 may be coupled to means for diverting a small portion of the forward power to a side branch. The means for diverting a small portion of the forward power to a side branch may be coupler 21. Coupler 21 may be, for example, a cross guide coupler, and may be more specifically by way of example a 20 dB cross guide coupler. The diversion of a portion of the forward power is used in properly calibrating the Hall effect probe to zero in the absence of an applied magnetic field. The side branch 22 has a single computer controlled variable attenuator 35 and computer controlled variable phase shifter 40 in order to produce a very small signal of the proper phase that can be used to make an ultra-fine correlation in zeroing the Hall effect probe in the absence of a magnetic field. As the variable attenuator and variable phase shifter are preferably-computer controlled, adjustments are facilitated. It will be understood that, in principle, the variable attenuator and phase shifter could be manually adjustable.

The main output of coupler 21 will be referred to as main branch 24. Main branch 24 preferably has a waveguide for transmission of microwave radiation to transition 25. Main branch 24 may include conventional rectangular waveguide 20. As shown in FIG. 2, reflected power detector 23 is shown in main branch 24. Reflected power detector 23 detects microwave power being transmitted from transition 25 toward coupler 21. Reflected power detector 23 detects power reflected from test items back into main branch 24.

As noted above, a circular waveguide is provided positioned to receive microwave radiation from source 15. Specifically, circular waveguide 50 is coupled through coupler 21 and main branch 24 to source 15. Conventional rectangular waveguide 20 is coupled via a matched transition 25 into circular waveguide 50. Circular waveguide 50 is a cylindrical waveguide with a circular cross-section. Circular waveguide 50 transmits only the TE11 mode of the radiation. Circular waveguide interface 25 is coupled to circular waveguide 50, shown, for example, in FIG. 2. The coupling of the circular waveguide 50 to conventional waveguide 20 must be calibrated carefully to minimize reflection and loss of signal strength. The calibration procedure is set forth below. Circular waveguide 50 is mounted on interface 25 perpendicular to the long axis of conventional waveguide 20. The calibration may be effected by adjustment of the position of circular waveguide 25 along its long axis relative to interface 25. In one embodiment, circular waveguide 50 is mounted in a threaded track on interface 25. A circular waveguide adjustment 55 is provided in the form of a handle that rotates circular waveguide 50, so that the vertical position of circular waveguide 50 may be adjusted.

A mount 60 is provided to hold a sample of sheet material at a measurement location where microwave radiation transmitted from the circular waveguide 50 is received. The sample may be a wafer or other conductive test material 59. Mount 60 may be in the form of a vacuum chuck. Short tuning adjustment 65 is provided to move mount 60 precisely. Mount 60 is adapted to hold a wafer or other material in sheet form at an end of circular waveguide 50 opposite to interface 25. A moving short 58 is provided on the opposite side of the wafer or other material from the opening of circular waveguide 50. The short 58 will be placed ¼ wavelength from the wafer or other material. Short 58 is in the form of a conductive sheet, such as a copper-covered circuit board.

As noted above, a detector 18 is positioned in source module 15 to detect the forward power before division into main branch 24 and side branch 22. A detector 23 is positioned in main branch 24 so as to detect reflected microwave power. The reflected radiation detected by detector 23 has the same polarization as the forward microwave radiation. Hall probe 70 is inserted in circular waveguide 50 positioned to detect Hall effect microwave radiation reflected from material positioned in the vacuum chuck. The Hall effect radiation has polarization perpendicular to the polarization of the incident wave. As discussed below, the calibration process provides that only the Hall effect radiation is detected by Hall detector 95.

Hall probe 70 is coupled through coaxial line 75 to an input of directional coupler 80. Directional coupler 80 may be a 20 dB directional coupler. The output of branch 22, after passing through the attenuator module and variable phase shifter, is connected to an input of directional coupler 80. The output of directional coupler 80 is coupled to Hall detector 95. The calibration process, as described below, provides that the Hall detector 95 detects only radiation having a polarization perpendicular to that of the forward radiation. This radiation detected by Hall detector 95 is thus Hall effect radiation reflected from a sample.

Figure 3:
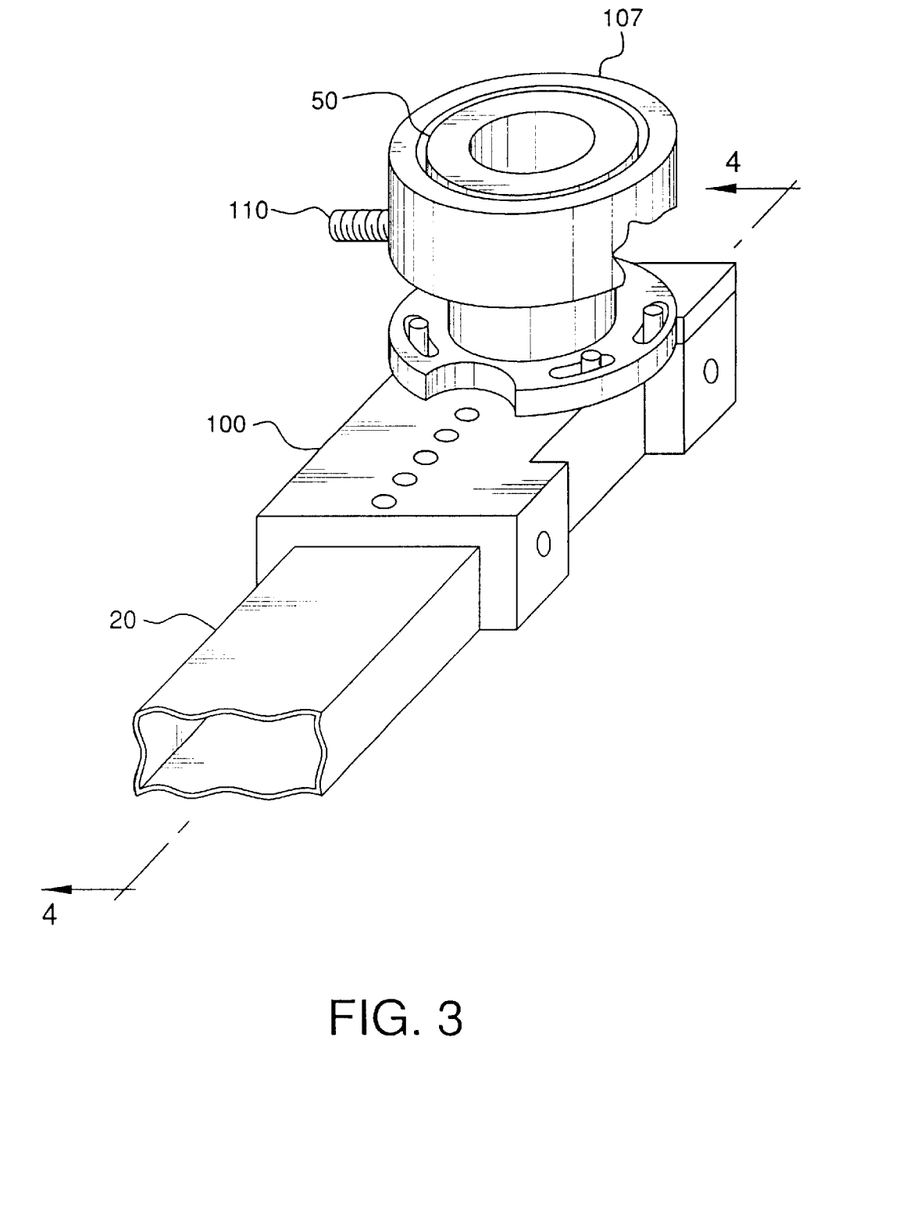
FIG. 3 is a view of a portion of an apparatus according to the invention.
Figure 4:
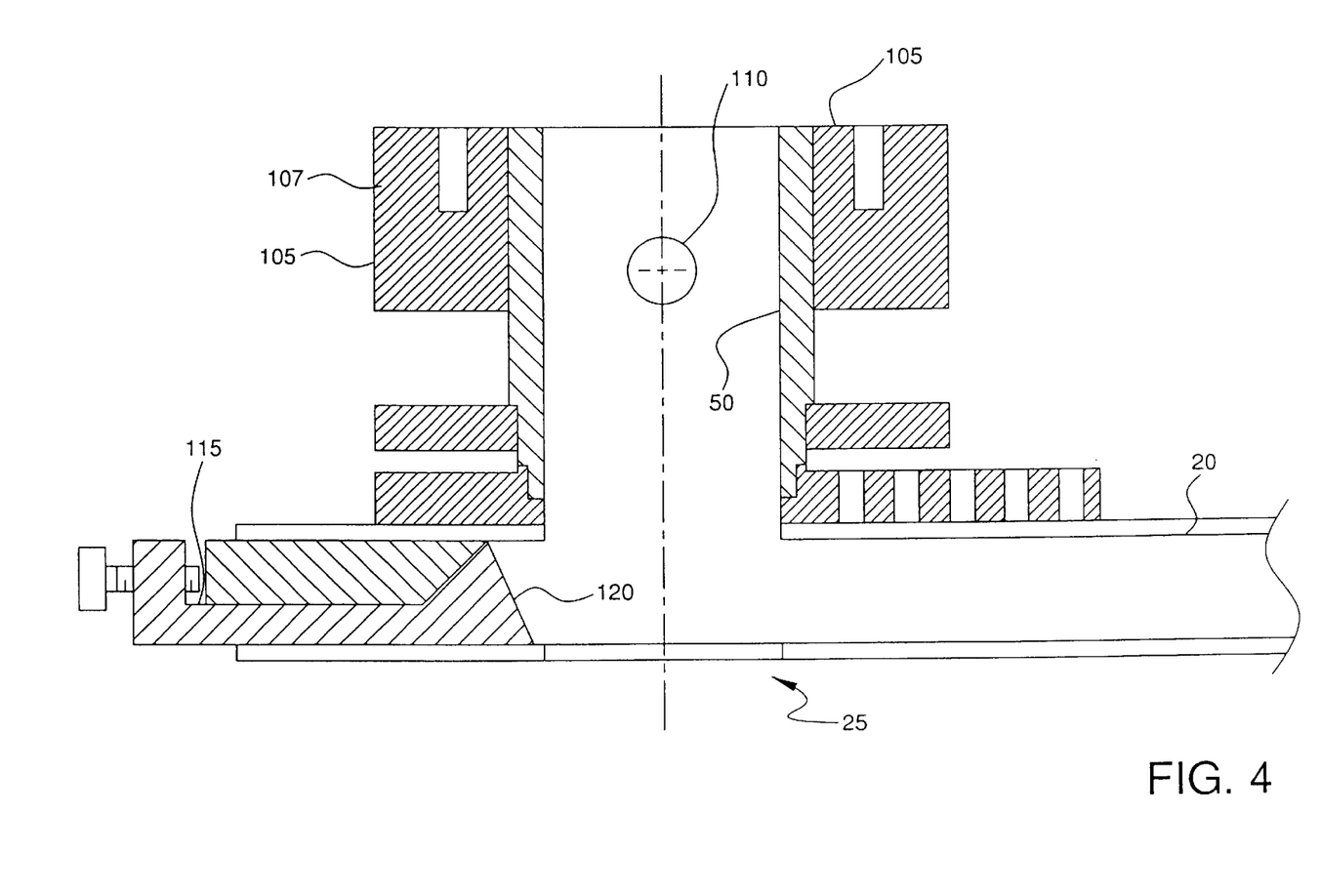
FIG. 4 is a cross-section of the apparatus of FIG. 3.

Details of an exemplary embodiment of the transition, circular waveguide, and mount will now be described. FIG. 3 is an isometric view, with partial cutaway, of interface 25. FIG. 4 is a sectional view along line 4—4 of FIG. 3. Interface 25 has a primary rectangular chamber 100 coupled at one end thereof to conventional waveguide 20. On an upper side of rectangular chamber 100 an aperture is provided to which circular waveguide 50 is attached. Interior to interface 25, opposite to conventional waveguide 20, there is provided a beam stop 115 completely filling an opening, and having a tapered face, preferably at an angle of 30 degrees to vertical, at 120. It will be appreciated that interface 25 may be modified by those of skill in the art by alternative designs to minimize reflection and loss at the interface between circular waveguide 50 and conventional waveguide 20. In FIGS. 3–4, it may be seen that circular waveguide 50 includes a probe flange 107 at an upper end thereof which has therein an opening for a probe at 110. A Hall probe may be inserted at 110.

Figure 5:
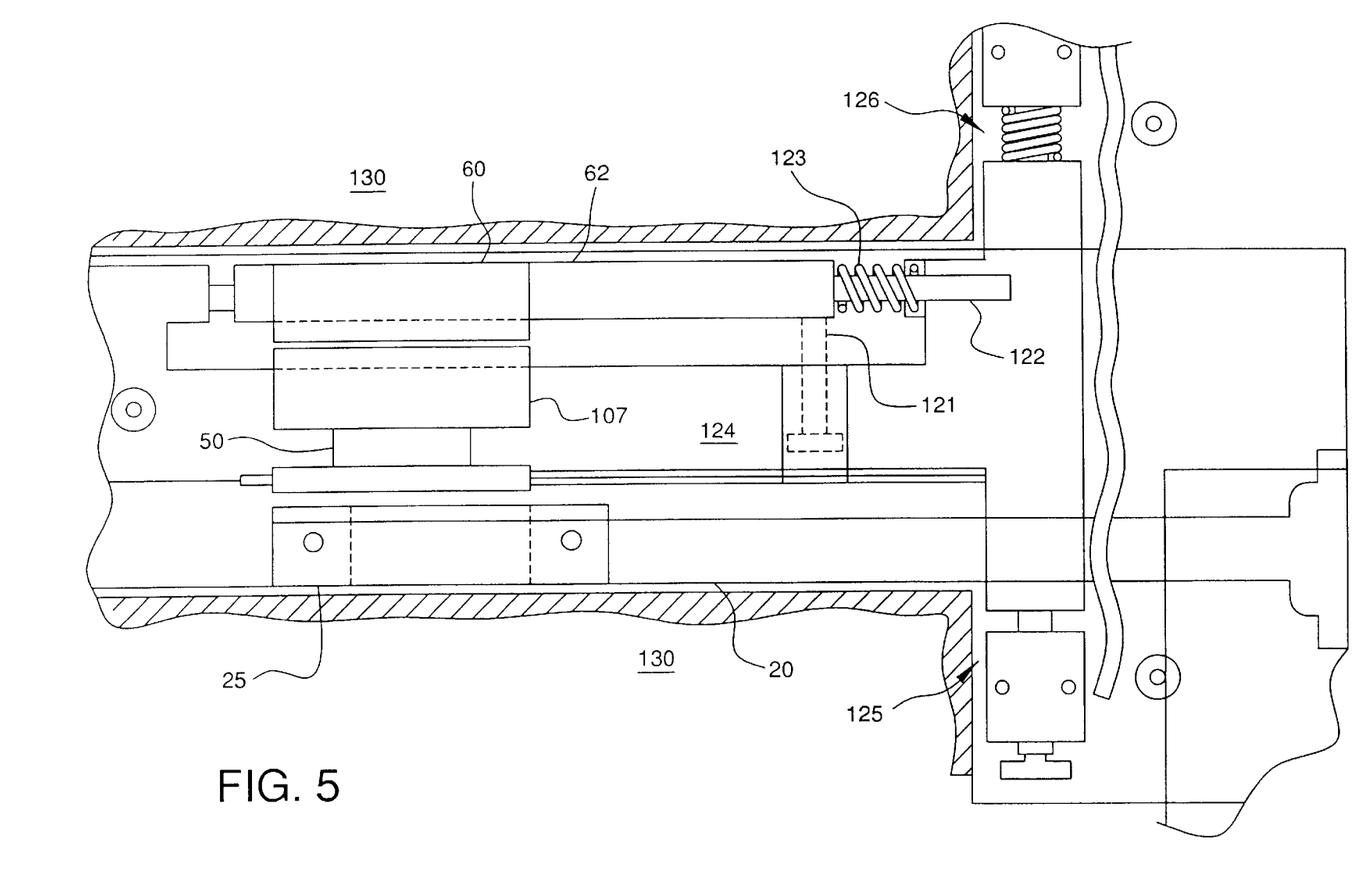
FIG. 5 is a view of an apparatus according to the invention.

FIG. 5 is a side view depicting an exemplary arrangement including circular waveguide 50, holder or mount 60, and related exemplary hardware. Holder or mount 60 serves to position a sheet material item to receive microwave radiation from circular waveguide 50. Conventional waveguide 20 is shown coupled to interface 25. Interface 25 is shown coupled to circular waveguide 50. Probe flange 107, located at an end of circular waveguide 50 opposite the coupling to interface 25, is opposite holder 60, in the form of a vacuum chuck. Vacuum chuck 60 is supported by an arm, which is chuck holder 62. Chuck holder 62 is supported by adjustable screws 121, 122, thereby permitting adjustment of the position of vacuum chuck 60 in two axes. Screws 121, 122 are supported on bridge 124, which is itself adjustably mounted as shown at 125, 126. Spring 123 may be provided on screw 122 to reduce the transfer of any vibrations in bridge 124. It will be understood that other configurations may be employed for the positioning of holder 60 relative to circular waveguide 50. FIG. 5 also shows generally the position of magnet 130 which provides the necessary magnetic field. The magnetic field is applied perpendicular to the plane of the wafer or other sample and along the long axis of circular waveguide 50. The design of one or more suitable magnets to provide the desired magnetic field strength is within the level of ordinary skill in the art. As noted below, in one example, the magnetic field strength at the wafer or other item positioned in the holder is desirably up to 9 kG.

The calibration and operation of the apparatus will now be discussed. This entire process may be carried out at room temperature. Room temperature is understood to include a range of temperatures at which humans may comfortably work. Room temperature excludes low temperatures, such as the boiling temperature of liquid nitrogen at atmospheric pressure. Voltmeters are preferably connected to the Hall detector cable, an input or forward power location, and a reflected power location. A gauss meter is provided to measure the intensity of the magnetic field. Commercial meters with RS232 or IEEE 488 bus communications are preferably used. A short 58, such as a copper coated PC board, is placed on the vacuum chuck and positioned. The computer controlled attenuation adjustment 35 is increased to a maximum. The position of the circular waveguide 50 is adjusted to obtain minimum voltage at Hall detector 95. While monitoring the Hall detector voltmeter, the computer controlled attenuation adjustment 35 is then adjusted, preferably automatically using the computer software, to bring detected voltage to a minimum. The computer controlled phase adjustment 40 is then adjusted, preferably automatically using the computer software, to obtain a minimum on the Hall detected voltage. The attenuation adjustment and phase adjustment are automatically adjusted using the computer software, to obtain a minimum here. The Hall detector voltage, forward detector voltage, and reflected detector voltage are recorded. The short is removed and replaced with the sample to be checked. The short tuning adjustment 65 of the vacuum chuck position is adjusted to obtain a minimum reflected power. The circular waveguide adjustment 55, attenuation adjustment 35 and phase adjustment 40 are all adjusted for a minimum on the Hall detector. The three voltages are then recorded for 0 magnetic field, and then at successive incrementally greater magnetic field strengths. The field strength ranges from 0–9 kG as a minimum. Preferably, the magnetic field is automatically varied using computer software that controls the magnet power supply to obtain the desired magnetic field. In principle, with further developments, significantly lower magnetic field strengths could be used in accordance with the method. The number of magnetic field values and the spacing between magnetic field values can be optimized to maximize analysis accuracy.

Figure 6:
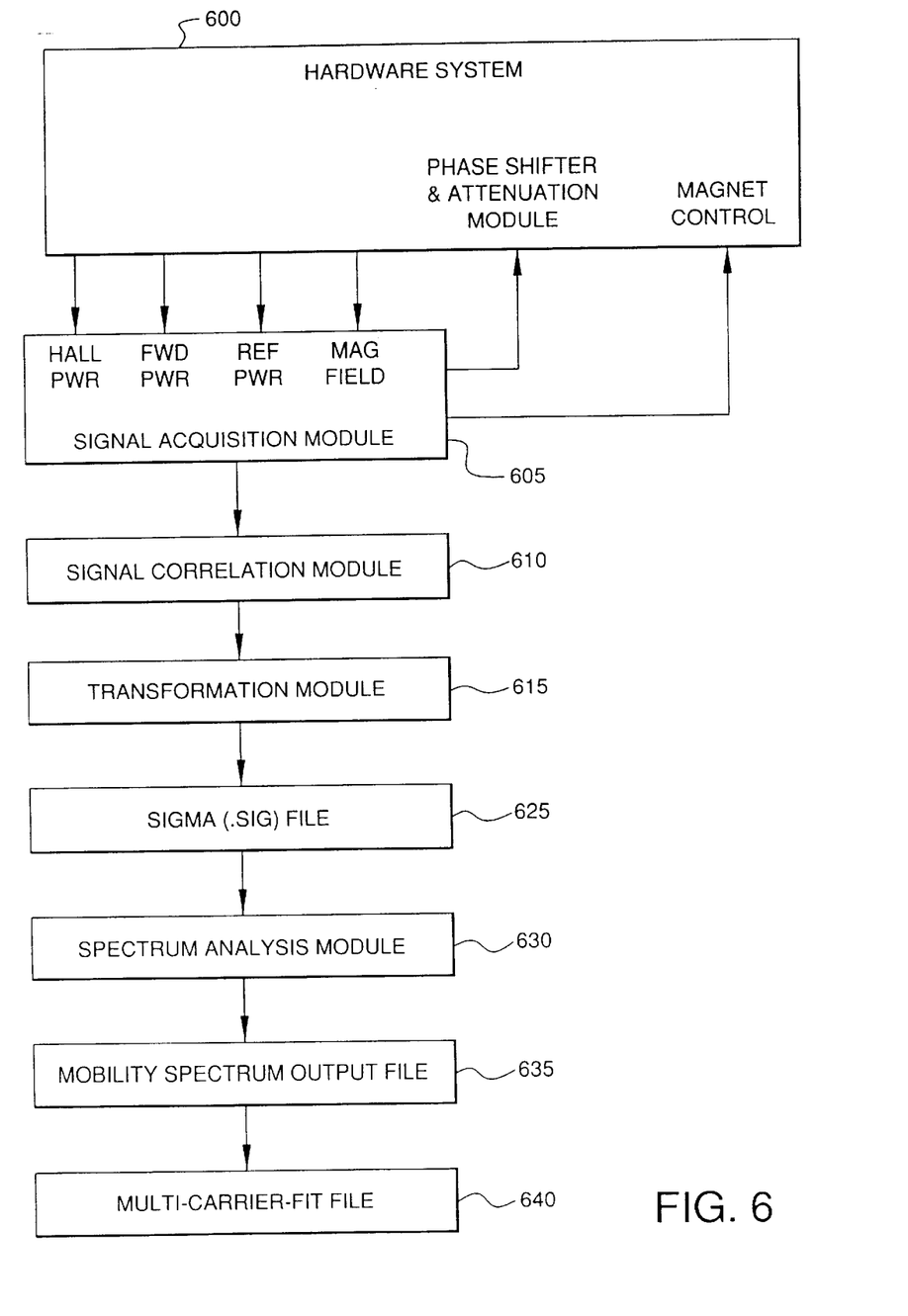
FIG. 6 is a flowchart of software used according to the invention.

The data are then interpreted to obtain mobility and sheet resistance readings. Referring to FIG. 6, an overview of the software is provided. The software may be written for a personal computer using an Intel Pentium or compatible chip as a processor, and the DOS or Windows operating systems. The hardware system described above is indicated generally by block 600. The first module, 605, is a signal acquisition and control module. This module receives signals from the detectors in the apparatus described above and controls the variable phase shifter and attenuator module as well as the magnet. The received signals are: Hall Power detection; Forward Power detection of Cu Short and Wafer; Reflected Power detection of Cu Short and Wafer; and Magnetic Field Strength detection. Those signals are passed through analog to digital converters and module 605 obtains values from the digital output. Once these signals are acquired the corresponding voltage input values are passed on to the Signal Correlation Module 610 for further processing.

Signal correlation module 610 receives inputs from the signal acquisition module 605 as raw input voltages. These voltages are input into algorithms to obtain values in correct engineering units. This step is a straightforward correlation.

The output of the signal correlation module 610 is received by the transformation module 615. The transformation module converts the output to Sigma Output file structure 625 which is then read by the Mobility Spectral Analysis Module 630. The Sigma Output file is composed of 14 lines of general test information, typically including the sample name, date, and similar information, followed by a line containing the sample thickness, followed by a line for each magnetic field at which Hall data was collected. Each of these data lines contain tab-separated entries for the magnetic field, Sigma_XX, SD_XX, Sigma_XY, and SD_XY, where SD_XX and SD_XY are the standard deviations for the Sigma_XX and Sigma_XY values, respectively. All entries are in MKSA units, i.e. thickness in meters, magnetic field in Tesla, and conductivities in Siemens/meter. This file is used as input for the Mobility Spectral Analysis Module in order to obtain the final mobility values and charge carrier densities. This module is composed of two separate program executables, which perform a variety of mathematical calculations in order to analyze magnetic field-dependent Hall data. These modules read input data from the Sigma Output file and generate a mobility spectrum output file 635 which includes a mobility spectrum whose peaks indicate the presence of discrete carrier types and a Multi-Carrier-Fit file 640 which includes the most likely mobility and charge carrier density values for those carrier types.

The only way to find solutions that are more precise or quantitative than the mobility spectrum peaks is to restrict the range of possible solutions by making assumptions about the carriers in the specimen. For example, the Multi-Carrier fitting technique makes the explicit assumption that there are a fixed number of carriers—each with a discrete mobility.

The calculations carried out by the software involve the following principles. When the microwave short at the back of the cavity behind the wafer is adjusted to the proper distance, the relationship between an amplitude reflection coefficient Γ, the sheet resistance of the wafer R, and the impedance Z of the circular waveguide for the $TE_{11}$ mode is:

$$\Gamma = (R-Z)/(R+Z)$$

For a circular waveguide of radius 1.045 cm, the impedance has been found to be 697.5 Ohm/square, which enables accurate measurement of a thin cap.

The microwave electric field at the wafer must be determined. The electric field amplitude in various axes, $E_x$, for example, are represented as $E_x=(1+\Gamma)(P_{incident}/A)^{1/2}$, and $E_y=(P_{Hall}/A)^{1/2}$. In the x direction, the amplitude is the sum of the incident and reflected wave amplitudes or the amplitude of the transmitted (standing) wave. For the y direction, the only propagating microwave signal is the Hall wave, which is generated at the wafer and detected in the reflected direction. The value A is a constant, which may be determined by integration across the circular cross section of the waveguide mode. The conductivity, $\sigma_{xx}$, or $\sigma_{xy}$, depending on the axis, can be represented, using these values, as $\sigma_{xx}=(1/Z)(1-\Gamma^2-F^2)/((1+\Gamma)^2+F^2)$, and as $\sigma_{xy}=(F/(2Z(1+\Gamma))) ((1+\Gamma)(3-\Gamma)-F^2)/((1+\Gamma)^2+F^2)$, where $F+E^-_{y1}/E^-_{x1}$. There is also a constant coefficient used to multiply the theoretical values of F since the currents that are locally perpendicular to the excited $TE_{11}$ mode do not couple exactly to the orthogonal $TE_{11}$ mode. The constant can be obtained by integration and has a value between 0 and 1. The previous analysis assumes that additional TE11 modes that are generated near the wafer are negligible. In some cases that is not valid. For those cases, a multi-mode analysis has been developed and can be used to determine Sigma__XX and Sigma__XY from the reflected microwave powers.

In order to obtain the mobility, the results of the calculations above are employed together with the detected magnetic field intensity B. For one carrier species in a single conductive layer, the carrier mobility is given by $\mu=(\sigma_{xy}/B)/\sigma_{xx}$.

The multi-carrier fitting procedure works as follows: First, the program determines the best fit for a single carrier using the Simplex method to minimize the least-squares deviation between the fitted and measured Hall data ($\sigma_{xx}$ and $\sigma_{xy}$). The uncertainty in each of the measured data is used to weight the terms in the least-squares sum and thereby obtain the most-likely solution. The uncertainties in the derived mobility and carrier density are estimated from the components of the Hessian matrix at the minimum (at the solution).

Next, the program determines the best fit using two carriers. The starting values for the Simplex procedure are obtained by displacing the previously-determined single carrier to slightly higher and lower mobilities. The Simplex procedure is identical to the procedure for a single carrier, except that there are now two mobilities to vary. The uncertainties in the derived parameters are again determined as in the description for a single carrier. The program also uses the statistical F-test to estimate the significance of the second carrier, i.e., it estimates whether addition of the second carrier improved the fit by enough to conclude that a second carrier probably exists. This is a very useful feature since it permits the user to estimate the number of statistically significant carriers that are present in the sample. The procedure continues, adding one carrier at a time and estimating the significance of the added carriers, until the number of carriers exceeds half the number of magnetic fields, at which point the procedure is terminated.

A summary of test results comparing the foregoing techniques to known destructive techniques, namely the contacted single magnetic field DC Hall technique, are set forth below:

TABLE

PHEMT TEST RESULT SUMMARY

|   | Mobility cm2/V-s | Sheet Charge X E12 carriers/cm2 |
|---|---|---|
| THIN CAP PHEMT SAMPLES | | |
| WAFER #1 | | |
| A | 5391 | 2.67 |
| B | 4721 | 2.848 |
| B | 4780 | 2.837 |
| B | 4753 | 2.859 |
|   | 4751.3 | 2.848 |
| STD | 24.115 | 0.00898146 |
| STD % | 0.508% | 0.315% |
| WAFER #2 | | |
| A | 5391 | 2.67 |
| B | 4721 | 2.831 |
| B | 4780 | 2.852 |
| B | 4753 | 2.827 |
|   | 4751.3 | 2.83666667 |
| STD | 24.115 | 0.01096459 |
| STD % | 0.508% | 0.387% |
| THICK CAP PHEMT SAMPLE | | |
| A | 7096 | 2.44 |
| B | 7783 | 1.46 |

A-CONTACTED SINGLE MAGNETIC FIELD DC HALL
B-NONCONTACT MULTIPLE MAGNETIC FIELD RF

Analysis software may be provided for use in non destructive, noncontact measurements of full semiconductor wafers or flat panel display materials for use by operators with minimal training. Experienced researchers are provided with the capability to perform in depth studies by varying readily accessible test parameters. Such test parameters include the magnetic field strength, the attenuation and phase of the microwave signal along the branch. The software also may provide graphic display including plots of the mobility spectra with conductivity and concentration as a function of mobility.

Plots of carrier concentration and mobility as a function of magnetic field may be displayed using a single carrier solution to the data of each field. The single carrier solution is used as a general check of the analysis; a sample with a single carrier should exhibit the same carrier concentration and mobility irrespective of the magnetic field. Conversely, a sample with more than one detectable carrier should exhibit variations as a function of the magnetic field.

All results may be displayed as sheet concentration numbers in the text window of the software. A calculation of the volumetric concentration of electrical carriers can be launched by checking the window of the result-screen of the software. If this operation is selected, the one-carrier solution is extracted by the multi-carrier technique and displayed in a separate window together with the entry fields for layer thickness and carrier type. This information is then used to calculate the depletion widths from the top surface and epi-substrate interfaces, so that the true thickness of the conductive layer can be obtained.

It will be appreciated that variations in mobility and carrier concentration across a layer may be obtained by conducting a test on a sample, then moving the sample in the mount in the plane perpendicular to the central axis of circular waveguide 50, and then repeating the test. This process may be repeated in order to obtain a map of mobility and carrier concentration.

While the invention has been described above with respect to particular embodiments, modifications and substitutions within the spirit and scope of the invention will be apparent to those of skill in the art.

What is claimed is:

1. A device for measurement of mobility and carrier concentration in conductive sheet materials, comprising:
   a microwave source;
   a circular waveguide positioned to receive microwave radiation from said microwave source;
   a mount adapted to position a sheet material item at a measurement location to receive microwave radiation transmitted from said circular waveguide;
   a magnet positioned to induce a magnetic field at the measurement location;
   a first detector to detect the power of the microwave radiation source;
   a second detector to detect the power of the microwave radiation reflected from a sheet material item in the measurement location;
   a third detector to detect a Hall effect microwave power.

2. The device of claim 1, further comprising a probe positioned in said circular waveguide, said probe being coupled to said third detector.

3. The device of claim 2, further comprising a directional coupler positioned to receive microwave radiation from said source, said directional coupler being coupled to a side branch and a main branch, said main branch being coupled to said circular waveguide, and said side branch being coupled to said third detector.

4. The device of claim 3, wherein said side branch is coupled through a variable attenuator and a variable phase shifter to said third detector.

5. The device of claim 1, further comprising calculating means for receiving data from said detectors and for calculating mobility and carrier concentration based on said data.

6. The device of claim 1, further comprising a conventional waveguide intermediate said microwave source and said circular waveguide, wherein said circular waveguide is adjustably positioned relative to said conventional waveguide.

7. The device of claim 6, wherein said second detector is positioned to detect reflected microwave field strength in said conventional waveguide.

8. The device of claim 1, further comprising a detector to detect magnetic field strength at the measurement location.

9. A method for measurement of mobility and carrier concentration in conductive sheet materials comprises the steps of:
   generating microwave radiation from a microwave source;
   transmitting only the TE11 mode of the generated microwave radiation successively to a conductive short and to a sheet material sample located at a measurement location;
   during said step of transmission, applying a magnetic field of a first selected intensity at the measurement location;
   repeating said step of applying a magnetic field employing a magnetic field of a second selected intensity;
   during said steps of transmitting and applying, detecting microwave field strength at a forward position;
   during said steps of transmitting and applying, detecting reflected microwave field strength reflected from each of the conductive short and the sample;
   during said steps of transmitting and applying, detecting Hall effect reflected microwave field strength;
   based on the detected microwave field strengths, calculating values for mobility and carrier concentration.

10. The method of claim 9, wherein said step of transmitting comprises transmitting microwave radiation through a circular waveguide.

11. The method of claim 10, wherein said step of detecting Hall effect reflected microwave field strength comprises providing a probe in said circular waveguide, and transmitting a signal from said probe to a coupler, simultaneously transmitting an attenuated and phase shifted portion of a signal from the microwave source to said coupler, and transmitting an output of said coupler to a detector.

12. The method of claim 10, wherein said step of transmitting comprises transmitting microwave radiation through a conventional waveguide to said circular waveguide.

13. The method of claim 12, wherein said step of detecting reflected microwave field strength comprises detecting said reflected microwave field strength at a detector positioned to detect microwave field strength in said conventional waveguide.

14. The method of claim 10, further comprising the step of adjusting a position of said circular waveguide while detecting microwave field values.

15. The method of claim 9, further comprising the step of detecting magnetic field strength simultaneously with said step of transmitting.

* * * * *